US009574969B2

(12) United States Patent
Bumgarner et al.

(10) Patent No.: US 9,574,969 B2

(45) Date of Patent: Feb. 21, 2017

(54) APPARATUSES FOR SCREEN TESTING AN OPTICAL FIBER AND METHODS FOR USING THE SAME

(71) Applicant: Corning Incorporated, Corning, NY (US)

(72) Inventors: Kirk Patton Bumgarner, Hampstead, NC (US); Aditya Kaimal, Wilmington, NC (US); Michael Terry Murphy, Oak Island, NC (US); Bruce Warren Reding, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/696,890

(22) Filed: Apr. 27, 2015

(65) Prior Publication Data

US 2015/0323434 A1 Nov. 12, 2015

Related U.S. Application Data

(60) Provisional application No. 61/990,793, filed on May 9, 2014.

(51) Int. Cl.

*G01N 3/08* (2006.01)
*G01M 11/08* (2006.01)

(Continued)

(52) U.S. Cl.

CPC ......... *G01M 11/088* (2013.01); *C03B 37/032* (2013.01); *G01M 11/30* (2013.01); *G01N 3/08* (2013.01)

(58) Field of Classification Search

CPC ...... G01M 11/30; G01M 11/088; G01N 3/08; C03B 37/02

See application file for complete search history.

(56) References Cited

U.S. PATENT DOCUMENTS

| | | | | |
|---|---|---|---|---|
| 3,323,492 A * | 6/1967 | Mellar | .................. | H01C 17/28 118/401 |
| 3,890,746 A * | 6/1975 | Saegusa | ................ | B24D 13/08 451/469 |

(Continued)

FOREIGN PATENT DOCUMENTS

| | | |
|---|---|---|
| EP | 0785173 | 7/1997 |
| JP | 05215640 | 8/1993 |

(Continued)

OTHER PUBLICATIONS

International Search Report, issued in connection with corresponding PCT application No. PCT/US2015/029688, Aug. 3, 2015.

(Continued)

*Primary Examiner* — Queenie Dehghan

(74) *Attorney, Agent, or Firm* — Kevin L. Bray

(57) ABSTRACT

In one embodiment, an apparatus for screen testing an optical fiber includes a fiber conveyance pathway, a capstan having an outer circumference and a fiber contact region extending around the outer circumference, the fiber contact region having a durometer hardness of less than or equal to about 40 Shore A, where the capstan is positioned adjacent to the fiber conveyance pathway such that when the optical fiber is directed over the fiber conveyance pathway, the optical fiber engages with the fiber contact region, and a pinch belt positioned adjacent to the fiber conveyance pathway such that the fiber conveyance pathway extends between the pinch belt and the fiber contact region, where the pinch belt is engageable with the fiber contact region such that, when the optical fiber is directed over the fiber conveyance pathway, the optical fiber is impinged between the pinch belt and the fiber contact region.

19 Claims, 14 Drawing Sheets

(51) Int. Cl.
*G01M 11/00* (2006.01)
*C03B 37/03* (2006.01)

(56) References Cited

U.S. PATENT DOCUMENTS

| | | | | |
|---|---|---|---|---|
| 4,997,276 | A | 3/1991 | Rochester et al. | |
| 5,178,313 | A | 1/1993 | LeCompte et al. | |
| 5,472,128 | A | 12/1995 | Nagayama et al. | |
| 5,644,669 | A * | 7/1997 | Oishi | G01M 11/088 385/123 |
| 5,647,884 | A * | 7/1997 | Overton | B65H 51/105 264/2.7 |
| 6,036,278 | A * | 3/2000 | Boyer | A63C 17/223 152/323 |
| 6,135,336 | A * | 10/2000 | Linderoth | B65H 51/10 226/108 |
| 6,834,553 | B2 | 12/2004 | Ravichandran et al. | |
| 6,881,166 | B1 * | 4/2005 | Burkhardt | F16H 55/50 474/166 |
| 2003/0011759 | A1 | 1/2003 | Ravichandran et al. | |
| 2008/0268999 | A1 * | 10/2008 | Kraft | F02B 67/06 475/185 |
| 2013/0255397 | A1 | 10/2013 | Bedarczyk et al. | |

FOREIGN PATENT DOCUMENTS

| | | | |
|---|---|---|---|
| JP | 07229820 | A * | 8/1995 |
| JP | 2005097051 | | 4/2005 |
| WO | 02052304 | | 7/2002 |

OTHER PUBLICATIONS

International Search Report and Written Opinion PCT/US2016/036175 Dated Sep. 16, 2016.

* cited by examiner

APPARATUSES FOR SCREEN TESTING AN OPTICAL FIBER AND METHODS FOR USING THE SAME

This application claims the benefit of priority under 35 U.S.C. §119 of U.S. Provisional Application Ser. No. 61/990,793 filed on May 9, 2014, the content of which is relied upon and incorporated herein by reference in its entirety.

BACKGROUND

Field

The present specification generally relates to screen testing fiber and, more specifically to apparatuses and methods for screen testing optical fiber.

Technical Background

Capstan assemblies used in the manufacture of optical fiber are typically used to draw the optical fiber from glass blanks that are mounted within draw towers, and/or for proof testing of the optical fiber, also known as fiber screening or screen testing. For consistency, the term screen testing will be used herein.

Capstan assemblies may include a capstan and a pinch belt between which the optical fiber is positioned. As the capstan is rotated, the friction generated between the capstan, the optical fiber, and the pinch belt pulls or draws the optical fiber from the associated glass blank through a series of related operations such as coating and sizing steps. When used in tandem, a pair of capstans can also be used to test the proof strength of the optical fiber by placing a tensile stress thereon.

During the screen test, the capstan and the pinch belt impose shear and compressive stresses on a coating of the optical fiber, and may cause damage to the coating, resulting in the optical fiber being discarded, thereby increasing manufacturing costs and reducing production yields.

Accordingly, a need exists for alternative screen testing apparatuses for limiting the effect of shear and compressive stresses imposed on the coating of an optical fiber.

SUMMARY

According to one embodiment, an apparatus for screen testing an optical fiber includes a fiber conveyance pathway, a capstan having an outer circumference and a fiber contact region extending around the outer circumference, the fiber contact region having a durometer hardness of less than or equal to about 40 Shore A, where the capstan is positioned adjacent to the fiber conveyance pathway such that when the optical fiber is directed over the fiber conveyance pathway, the optical fiber engages with the fiber contact region of the capstan, and a pinch belt positioned adjacent to the fiber conveyance pathway such that the fiber conveyance pathway extends between at least a portion of the pinch belt and the fiber contact region of the capstan, wherein the pinch belt is engageable with the fiber contact region of the capstan such that, when the optical fiber is directed over the fiber conveyance pathway, the optical fiber is impinged between the pinch belt and the fiber contact region of the capstan.

In another embodiment, an apparatus for screen testing an optical fiber including a fiber conveyance pathway, a capstan having an outer circumference and a fiber contact region extending around the outer circumference, the fiber contact region having a durometer hardness of less than or equal to about 40 Shore A, the fiber contact region including an inner layer of resilient material positioned on the outer circumference of the capstan, an outer layer of wear-resistant material positioned over the inner layer of resilient material, the outer layer of wear-resistant material having a durometer hardness of less than or equal to about 90 Shore A, and a pinch belt positioned adjacent to the fiber conveyance pathway such that the fiber conveyance pathway extends between at least a portion of the pinch belt and the fiber contact region of the capstan, where the pinch belt is engageable with the fiber contact region of the capstan such that, when the optical fiber directed over the fiber conveyance pathway, the optical fiber is impinged between the pinch belt and the fiber contact region of the capstan.

In yet another embodiment, a method for screen testing an optical fiber includes directing an optical fiber on a fiber conveyance pathway, directing the optical fiber around a capstan, the capstan having an outer circumference and a fiber contact region extending around the outer circumference, the fiber contact region including an inner layer of resilient material positioned on the outer circumference of the capstan, an outer layer of wear-resistant material positioned over the inner layer of resilient material, the outer layer of wear-resistant material having a durometer hardness of less than or equal to 90 Shore A, wherein the fiber contact region has a durometer hardness of less than or equal to 40 Shore A, and impinging the optical fiber between a pinch belt positioned adjacent to the fiber conveyance pathway and the fiber contact region of the capstan, wherein the fiber contact region elastically deforms and the optical fiber is depressed into the fiber contact region of the capstan.

Additional features and advantages of the apparatuses and methods for screen testing an optical fiber described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
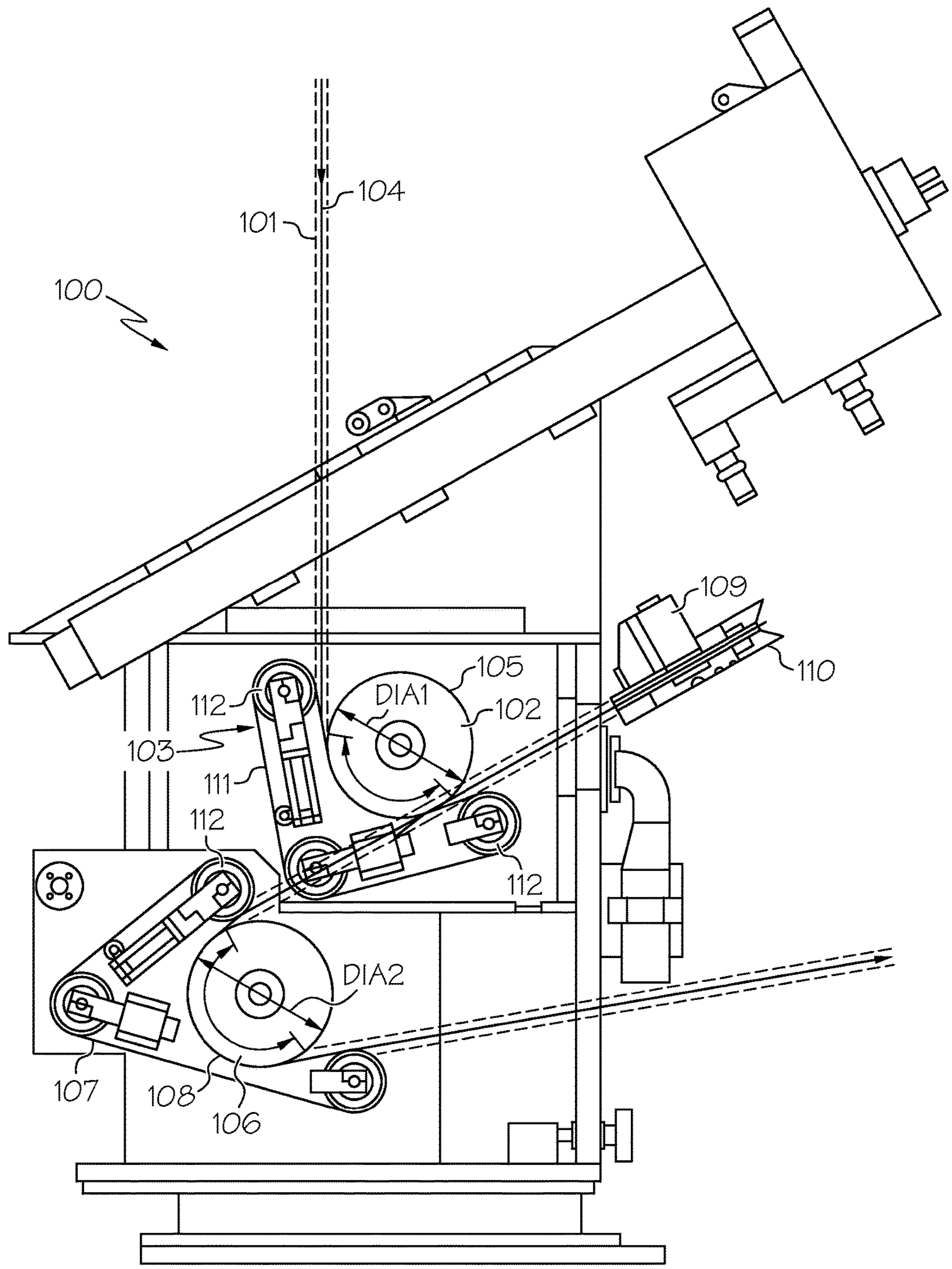
FIG. 1 schematically depicts a perspective view of an apparatus for screen testing an optical fiber including a capstan and a pinch belt according to one or more embodiments shown or described herein.

Reference will now be made in detail to embodiments of the apparatuses and methods for screen testing an optical fiber described herein, examples of which are illustrated in the accompanying drawings. Whenever possible, the same reference numerals will be used throughout the drawings to refer to the same or like parts. In one embodiment, an apparatus for screen testing an optical fiber includes a fiber conveyance pathway, a capstan having an outer circumference and a fiber contact region extending around the outer circumference, the fiber contact region having a durometer hardness of less than or equal to about 40 Shore A, where the capstan is positioned adjacent to the fiber conveyance pathway such that when the optical fiber is directed over the fiber conveyance pathway, the optical fiber engages with the fiber contact region of the capstan, and a pinch belt positioned adjacent to the fiber conveyance pathway such that the fiber conveyance pathway extends between at least a portion of the pinch belt and the fiber contact region of the capstan, wherein the pinch belt is engageable with the fiber contact region of the capstan such that, when the optical fiber is directed over the fiber conveyance pathway, the optical fiber is impinged between the pinch belt and the fiber contact region of the capstan. Methods and apparatuses for screen testing optical fiber will be described in more detail herein with specific reference to the appended drawings.

Optical fibers may be formed by drawing a thin glass fiber from a glass blank or "preform." After the optical fiber is drawn from the glass blank, one or more coatings may be applied to the glass fiber to protect the glass and preserve the structural integrity of the optical fiber. To form optical fiber having an extended length, a plurality of optical fibers may be consecutively spliced together. To splice together a pair of optical fibers, the one or more coatings are stripped from the glass fibers near the ends that are to be joined together. The ends of the two glass fibers are joined together, and a re-coat coating may be applied to the optical fiber to replace the stripped coatings.

The re-coat coating applied to replace the stripped coatings may have a different compressive and shear modulus than the one or more coatings of the original optical fibers. In particular, the re-coat coating may have a higher compressive modulus and a higher shear modulus than the one or more coatings on the original optical fibers. Because the re-coat coating has a higher compressive modulus and shear modulus than the one or more coatings of the optical fibers, the re-coat coating may exhibit less elastic deformation under compressive forces and shear forces imposed by the capstan and pinch belt. Because the re-coat coating deforms less than the one or more coatings of the original optical fibers under the compressive and shear forces imposed by the capstan and pinch belt, stress may be placed on the optical fiber at the interface between the re-coat coating and the one or more coatings of the original optical fibers. The stress placed on the optical fiber may lead to cohesive failure at the interface between the re-coat coating and the one or more coatings of the optical fiber. The stress placed on the optical fiber may also lead to adhesive failure between the one or more coatings and the glass fiber. Additionally, the stress placed on the optical fiber may damage an outer surface of the one or more coatings. Accordingly, the stress placed on the optical fiber may damage the coatings of the optical fiber, leading to optical fiber being discarded, increasing manufacturing costs.

The apparatuses and methods described herein reduce the compressive and shear stress imposed on an optical fiber directed between at least one capstan and at least one pinch belt during a screen test of the optical fiber. Reducing the compressive and shear stress imposed on an optical fiber during a screen test of the optical fiber may reduce the likelihood of cohesive failure of the coatings of the optical fiber.

Referring to FIG. 1, one embodiment of a screen testing apparatus 100 for screen testing an optical fiber is schematically depicted. The screen testing apparatus 100 generally includes a fiber conveyance pathway 101 that extends through the screen testing apparatus 100. The fiber conveyance pathway 101 of the screen testing apparatus 100 defines a pathway over which an optical fiber is directed during the screen test. The screen testing apparatus 100 generally includes at least a first capstan 102 positioned adjacent to a fiber conveyance pathway 101 and at least a first pinch belt 103 positioned adjacent to the fiber conveyance pathway 101 opposite the first capstan 102. The first capstan 102 and the first pinch belt 103 are positioned so that the fiber conveyance pathway 101 is positioned between the first capstan 102 and the first pinch belt 103. As an optical fiber 104 is directed over the fiber conveyance pathway 101, the first pinch belt 103 impinges the optical fiber 104 between the first pinch belt 103 and the first capstan 102.

The first capstan 102 has a first diameter DIA1, and an outer circumference 105. The outer circumference 105 of the first capstan 102 is positioned adjacent to the fiber conveyance pathway 101 so that the optical fiber 104 directed over the fiber conveyance pathway 101 engages the outer circumference 105 of the first capstan 102.

The screen testing apparatus 100 may optionally include a second capstan 106 positioned adjacent to the fiber conveyance pathway 101 and a second pinch belt 107 positioned adjacent to the fiber conveyance pathway 101. Similar to the first capstan 102 and the first pinch belt 103, the second capstan 106 and the second pinch belt 107 may be positioned so that the fiber conveyance pathway 101 is positioned between the second capstan 106 and the second pinch belt 107. As the optical fiber 104 is directed over the fiber conveyance pathway 101, the second pinch belt 107 impinges the optical fiber 104 between the second pinch belt 107 and the second capstan 106.

The second capstan 106 may have a second diameter DIA2, and an outer circumference 108. The outer circumference 108 of the second capstan 106 is positioned adjacent to the fiber conveyance pathway 101 so that an optical fiber 104 directed over the fiber conveyance pathway 101 engages the outer circumference 108 of the second capstan 106.

The screen testing apparatus 100 may optionally include a load cell 109 and a pulley 110 positioned adjacent to the fiber conveyance pathway 101. The load cell 109 and the pulley 110 are positioned adjacent to the fiber conveyance pathway 101 between the first capstan 102 and the second capstan 106. The pulley 110 may be positioned adjacent to the fiber conveyance pathway 101 so that the pulley contacts the optical fiber 104 directed over the fiber conveyance pathway 101. The load cell 109 may be coupled to the pulley 110 so that the load cell detects a tension in the optical fiber 104 through the contact between the optical fiber 104 and the pulley 110.

To rotate the first capstan 102 and the second capstan 106, the first capstan 102 may be connected to a first driveshaft (not depicted) and the second capstan 106 may be connected to a second driveshaft (not depicted) that is driven independent of the first driveshaft. The first driveshaft and the second driveshaft may be driven by power sources which may include without limitation, electric motors, pneumatically driven spindles, and the like.

The first capstan 102 and the second capstan 106 apply a tensile stress on the optical fiber 104 directed over the fiber conveyance pathway 101. To apply a tensile stress on the optical fiber 104, the first capstan 102 and the second capstan 106 may be rotated at different rotational speeds. More specifically, the second capstan 106 may be rotated at a higher rotational speed than the first capstan 102. As a result of the higher rotational speed of the second capstan 106, a portion of the optical fiber 104 between the first capstan 102 and the second capstan 106 on the fiber conveyance pathway 101 will be under tension.

Alternatively, to apply a tensile stress to the optical fiber, the diameter DIA2 of the second capstan 106 may be selected to be larger than the diameter DIA1 of the first capstan 102. When the rotational speed of the second capstan 106 is the same or higher than the rotational speed of the first capstan 102, and the diameter DIA2 of the second capstan 106 is greater than the diameter DIA1 of the first capstan 102, a linear speed of the outer circumference 108 of the second capstan 106 will be higher than a linear speed of the outer circumference 105 of the first capstan 102. As a result of the higher linear speed of the outer circumference 108 of the second capstan 106, the portion of the optical fiber 104 between the first capstan 102 and the second capstan 106 on the fiber conveyance pathway 101 will be under tension.

Figure 2:
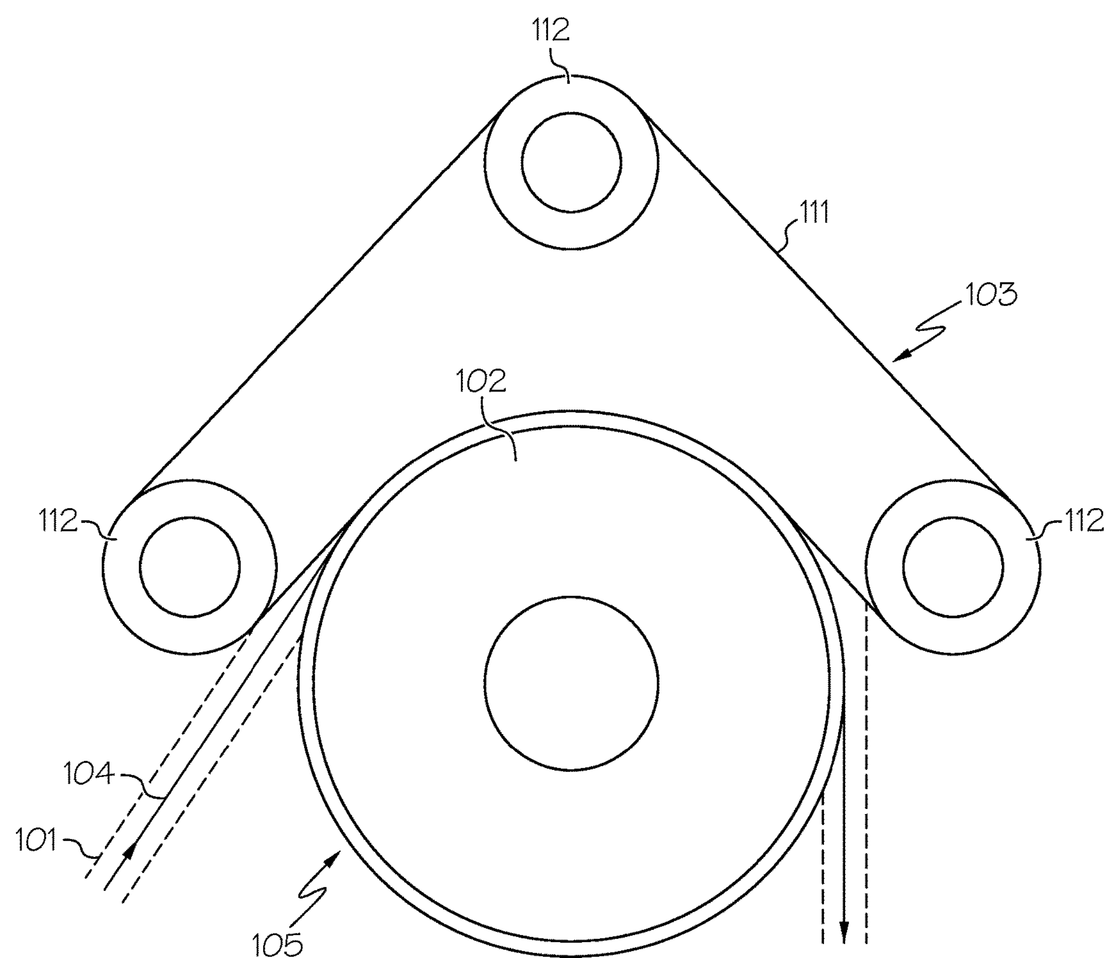
FIG. 2 schematically depicts a capstan and pinch belt according to one or more embodiments shown or described herein.

Referring now to FIGS. 1 and 2, to isolate the tension applied to the optical fiber 104 by the first capstan 102 and the second capstan 106, the first pinch belt 103 impinges the optical fiber 104 between the first pinch belt 103 and the first capstan 102. In embodiments, the first pinch belt 103 may include a first belt 111 and a plurality of idler pulleys 112 that are positioned adjacent to the fiber conveyance pathway 101. The first belt 111 is positioned around the plurality of idler pulleys 112 so that the first belt 111 impinges the optical fiber 104 directed over the fiber conveyance pathway 101 between the first belt 111 and the first capstan 102. Accordingly, the first pinch belt 103 applies a compressive force to the optical fiber 104 between the first pinch belt 103 and the first capstan 102 to isolate the tension applied to the optical fiber 104 between the first capstan 102 and the second capstan 106. In embodiments, the position of the plurality of idler pulleys 112 may be adjustable, such that a tension in the first belt 111 and, accordingly, the compressive force applied to the optical fiber 104, may be adjusted. To adjust the position of the idler pulleys 112, the idler pulleys may be coupled to the screen testing apparatus by actuators, such as pneumatic devices, electric motors, and the like. While reference has been made hereinabove to the configuration of the first pinch belt 103 and the first capstan 102, it should be understood that the second pinch belt 107 and the second capstan 106 may likewise include a plurality of adjustable idler pulleys 112 to isolate the tension in the optical fiber 104 between the first capstan 102 and the second capstan 106.

Figure 3:
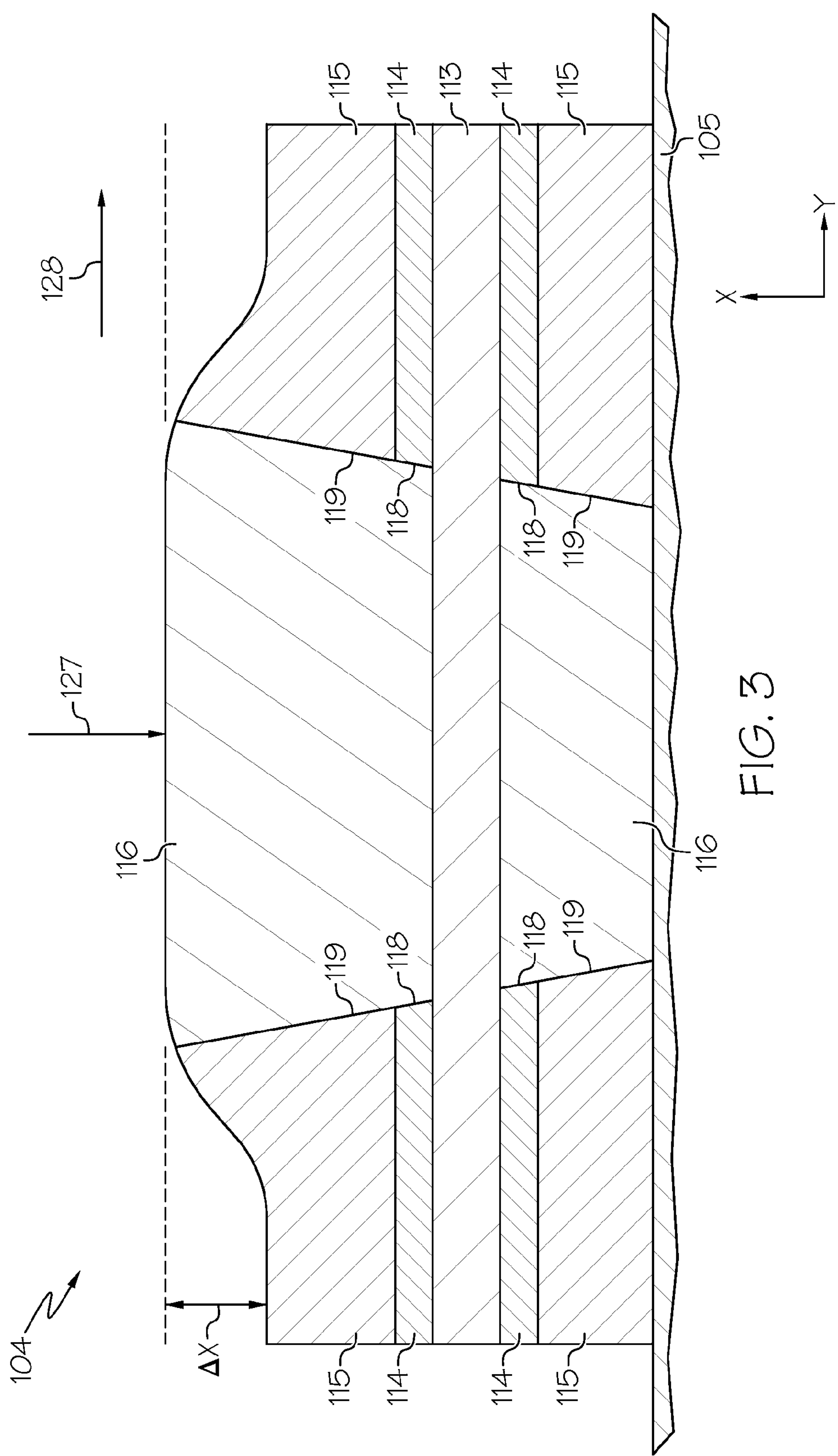
FIG. 3 schematically depicts a cross-sectional view of a coated optical fiber under compressive stress.

Referring to FIG. 3, a cross-section of an optical fiber 104 is depicted under compressive force 127, such as the compressive force applied to the optical fiber 104 by the first pinch belt 103 and the first capstan 102. In particular, FIG. 3 depicts the compressive force 127 applied to the optical fiber 104 by the first pinch belt 103 and the first capstan 102, as the optical fiber 104 is impinged between the first pinch belt 103 and the outer circumference 105 of the first capstan 102. A conveyance direction 128 of the fiber conveyance pathway 101 may extend in a direction generally tangential to the outer circumference 105 of the first capstan 102 (i.e., in the +/−Y direction in the coordinate axis depicted on FIG. 3). The compressive force 127 may be generally applied in a direction perpendicular to the conveyance direction 128 (i.e., in the +/−X direction in the coordinate axis depicted on FIG. 3).

The optical fiber 104 may include a glass fiber 113, a primary coating 114, a secondary coating 115, and a re-coat coating 116. The primary coating 114 may be positioned over the glass fiber 113, and the secondary coating 115 may be positioned over the primary coating 114. Proximate to a location where the optical fiber 104 has been spliced together, a re-coat coating 116 may be positioned over the glass fiber 113 and extend radially outward from the glass fiber 113. The re-coat coating 116 may form an interface 118 with the primary coating 114 and an interface 119 with the secondary coating 115 in an axial direction so that the glass fiber 113 is encapsulated by the primary coating 114, the secondary coating 115 and the re-coat coating 116.

To maintain the structural integrity of the optical fiber 104, the secondary coating 115 may comprise a wear-resistant material selected to have a high shear modulus and a high compressive modulus. The primary coating 114 may be selected to have a low shear modulus and a low compressive modulus to provide the optical fiber 104 with flexibility. Because the re-coat coating 116 comprises a single layer, the re-coat coating 116 may comprise a material selected to have a high shear modulus and a high compressive modulus to maintain the structural integrity of the optical fiber 104 at the location where the optical fiber 104 has been spliced.

Still referring to FIG. 3, the optical fiber 104 with a re-coat coating 116 is depicted under a compressive force 127. Because the primary coating 114 has a low compressive modulus and the re-coat coating 116 has a high compressive modulus, the primary coating 114 elastically deforms more than the re-coat coating 116 under the same compressive force 127. Because the primary coating 114 elastically deforms more than the re-coat coating 116, the optical fiber 104 will deflect more at portions of the optical fiber 104 including primary coating 114 than the optical fiber 104 deflects at portions of the optical fiber 104 including a re-coat coating 116. The difference in the deflection $\Delta X$ of the optical fiber 104 at portions including a primary coating 114 and portions including a re-coat coating 116 creates stress at the interface 118 between the primary coating 114 and the re-coat coating 116. The stress at the interface 118 between the primary coating 114 and the re-coat coating 116 may lead to cohesive failure between the primary coating 114 and the re-coat coating 116 at the interface 118 exposing the glass fiber to environmental conditions which may degrade the optical fiber, the performance of the optical fiber, or even lead to failure of the optical fiber.

Figure 4:
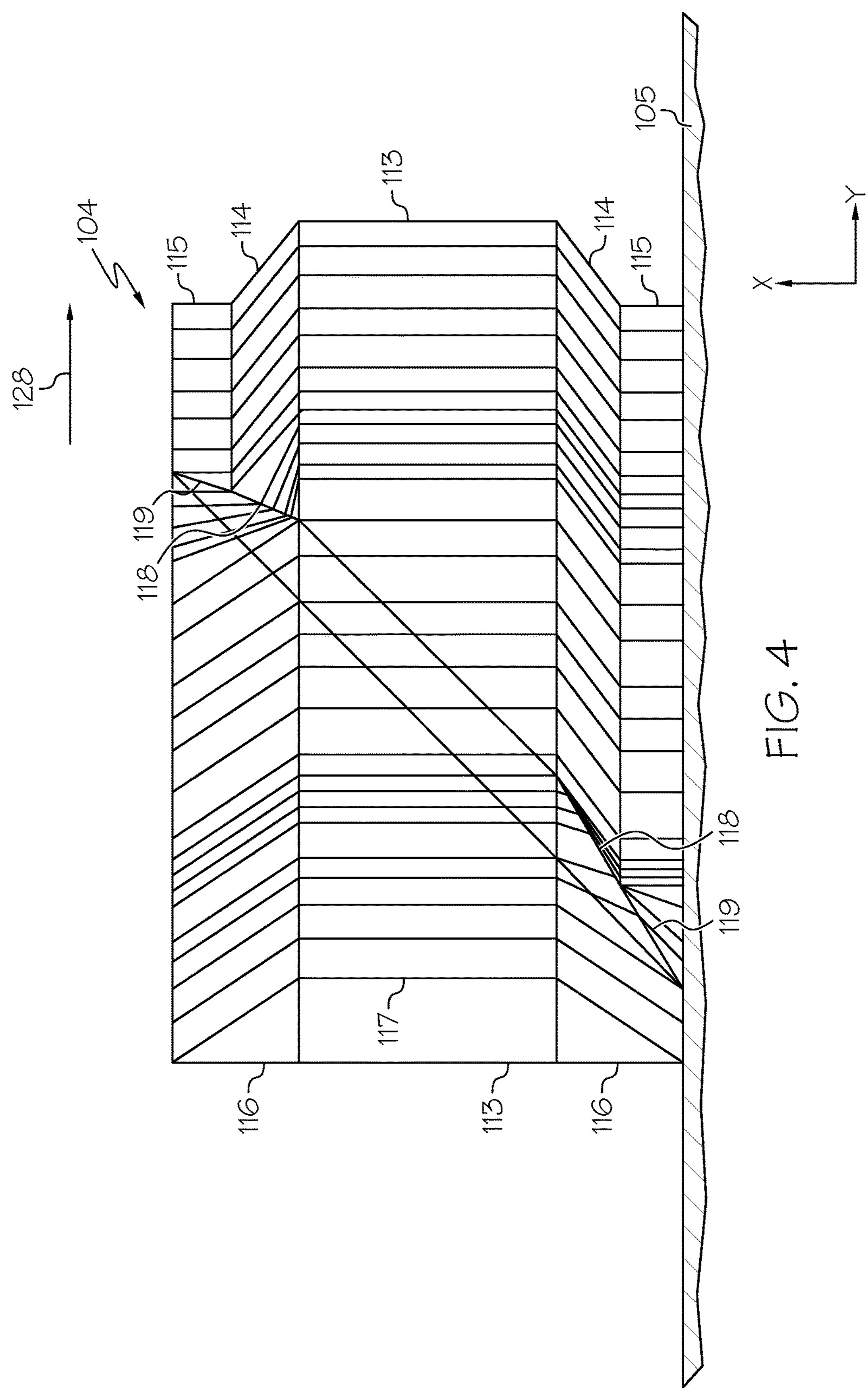
FIG. 4 schematically depicts a cross-sectional view of a coated optical fiber under shear stress.

Referring to FIG. 4, an optical fiber 104 is depicted under shear stress, such as the shear stress applied to the optical fiber 104 by the screen testing apparatus 100 at the first capstan 102. For illustrative purposes, a series of lines 117 are depicted in the optical fiber 104 to illustrate the strain in the portions of the optical fiber 104. As discussed hereinabove, the first capstan 102 and the second capstan 106 may apply a tensile force to the optical fiber 104 during a screen test, and the tensile force may be isolated by impinging the optical fiber 104 between the first pinch belt 103 and the first capstan 102. The tensile force may be applied in a direction generally tangential to the outer circumference 105 of the first capstan 102 (i.e., in the +/−Y direction in the coordinate axis depicted on FIG. 4). Because the primary coating 114 of the optical fiber 104 has a low shear modulus and the re-coat coating 116 has a high shear modulus, the primary coating 114 elastically deforms more than the re-coat coating 116 under the same tensile force. Because the primary coating 114 elastically deforms more than the re-coat coating 116, the optical fiber 104 will deflect more at portions of the optical fiber 104 including the primary coating 114 than the optical fiber 104 deflects at portions of the optical fiber 104 including only the re-coat coating 116. The difference in the deflection of the optical fiber 104 at portions including a primary coating 114 and the deflection at portions including a re-coat coating 116 creates stress at the interface 118 between the primary coating 114 and the re-coat coating 116. The stress at the interface 118 between the primary coating 114 and the re-coat coating 116 may lead to cohesive failure between the primary coating 114 and the re-coat coating 116 at the interface 118.

Figure 5C:
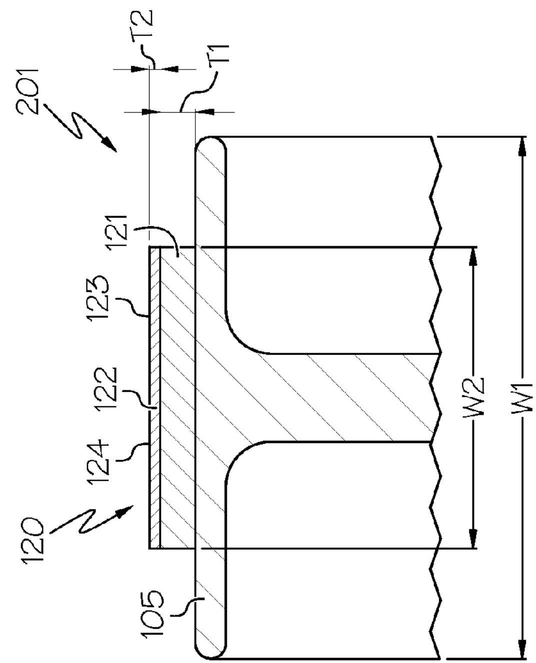
FIG. 5C schematically depicts an enlarged view of a portion of a cross-section of a capstan according to one or more embodiments shown or described herein.
Figure 5B:
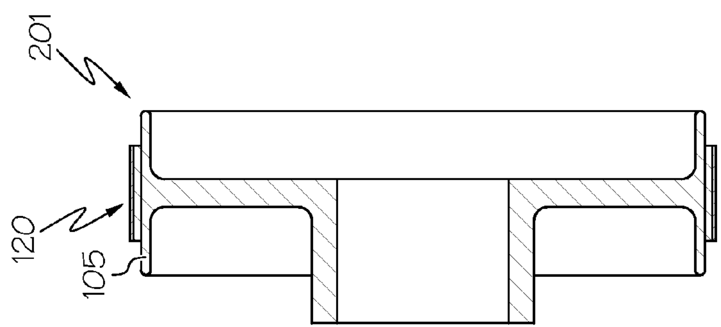
FIG. 5B schematically depicts a front-view cross section of a capstan according to one or more embodiments shown or described herein.
Figure 5A:
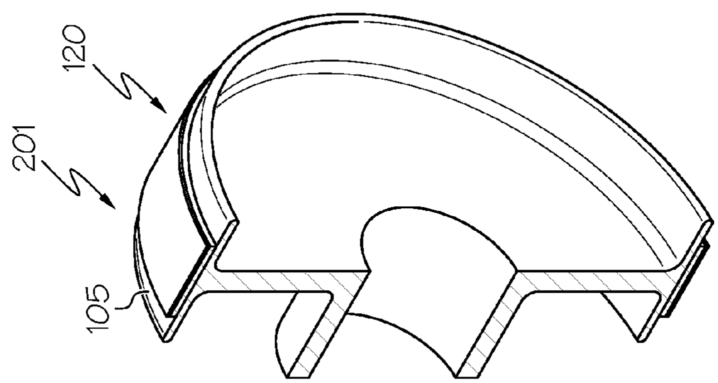
FIG. 5A schematically depicts a perspective cross-sectional view of a capstan according to one or more embodiments shown or described herein.

To reduce the compressive and shear stress placed on the optical fiber 104 during the screen testing process, various embodiments of capstans which may be used as the first capstan 102 and/or the second capstan 106 are described herein. Referring to FIGS. 5A, 5B, and 5C, one embodiment of a capstan 201 is depicted. The capstan 201 is generally cylindrical, and has a diameter DIA1, a width W1, and an outer circumference 105. The outer circumference 105 of the first capstan 102 includes a fiber contact region 120 extending around the outer circumference 105 of the capstan 201. The fiber contact region 120 of the capstan 201 may be the portion of the outer circumference 105 of the capstan 201 that engages the optical fiber 104 directed over the fiber conveyance pathway 101. The fiber contact region 120 of the capstan 201 has a durometer hardness of less than or equal to about 40 Shore A. In embodiments, the fiber contact region 120 may have a width W2 that is greater than or equal to about ten times a diameter of an optical fiber 104 directed over the fiber conveyance pathway 101.

In this embodiment, the fiber contact region 120 may comprise an inner layer 121. The inner layer 121 of the fiber contact region 120 may be positioned over the outer circumference 105 of the capstan 201, extending around the outer circumference 105 of the capstan 201. The inner layer 121 of the fiber contact region 120 has a thickness T1 extending radially outward from the outer circumference 105 of the capstan 201 to an outer circumference 122 of the inner layer 121. In embodiments, the thickness T1 of the inner layer may be greater than or equal to about 1 mm and less than or equal to about 12 mm. In an alternative embodiment, the thickness T1 of the inner layer may be greater than or equal to about 1 mm and less than or equal to about 5 mm.

The inner layer 121 of the fiber contact region 120 may be formed from a resilient material. The resilient material of the inner layer 121 may be selected to have a desired hardness and a desired compressive modulus and shear modulus to reduce the compressive and shear stresses on the optical fiber 104 contacting the fiber contact region 120. In embodiments, the resilient material of the inner layer 121 is selected to have a durometer hardness of less than or equal to about 35 Shore A. In another embodiment, the resilient material may be selected to have a durometer hardness of less than or equal to about 20 Shore A.

In embodiments, the resilient material of the inner layer 121 may be an isotropic material, where the durometer hardness of the material correlates to a compressive modulus and a shear modulus of the material. More specifically, a higher durometer hardness value of the resilient material of the inner layer 121 may correlate to a higher compressive modulus and a higher shear modulus of the resilient material. Conversely, a lower durometer hardness value of the resilient material of the inner layer 121 may correlate to a lower compressive modulus and a lower shear modulus of the resilient material. As will be described in greater detail herein, a low durometer hardness value, and consequently a low compressive modulus and shear modulus of the resilient material of the inner layer 121 may reduce the compressive and shear stress in the optical fiber 104 in contact with the fiber contact region 120.

In embodiments, the resilient material of the inner layer 121 may also be selected to have a shear modulus and a compressive modulus of less than or equal to about 1 MPa. In another embodiment, the resilient material of the inner layer 121 may be selected to have a shear modulus and a compressive modulus greater than or equal to about 0.1 MPa and less than or equal to about 0.5 MPa. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101.

The fiber contact region 120 of the capstan 201 may further include an outer layer 123 positioned over the inner layer 121. In embodiments, the outer layer 123 may extend laterally in a width direction to cover the inner layer 121 of the fiber contact region 120. The outer layer 123 may have a thickness T2 extending radially outward from the outer circumference 122 of the inner layer 121 to an outer circumference 124 of the outer layer 123. The thickness T2 of the outer layer 123 may be greater than or equal to about 10 μm and less than or equal to about 250 μm. In alternative embodiments, the thickness T2 of the outer layer 123 may be greater than or equal to about 30 μm and less than or equal to about 250 μm. In still other embodiments, the thickness T2 of the outer layer 123 may be greater than or equal to about 10 μm and less than or equal to about 300 μm. In further embodiments, the thickness T2 of the outer layer 123 may be greater than or equal to about 30 μm and less than or equal to about 300 μm. In another embodiment, the thickness T2 of the outer layer 123 may be greater than or equal to about 10 μm and less than or equal to about 350 μm. In yet another embodiment, the thickness T2 of the outer layer 123 may be greater than or equal to about 30 μm and less than or equal to about 350 μm.

The outer layer 123 of the fiber contact region 120 may be formed from a wear-resistant material. The wear-resistant material of the outer layer 123 may be selected to have a desired hardness and a desired compressive modulus and shear modulus. In one embodiment, the wear-resistant material of the outer layer 123 may be selected to have a durometer hardness greater than or equal to about 55 Shore A and less than or equal to about 90 Shore A. In another embodiment, the wear-resistant material of the outer layer 123 may be selected to have a durometer hardness greater than or equal to about 65 Shore A and less than or equal to about 80 Shore A.

Similar to the resilient material of the inner layer 121, the wear-resistant material of the outer layer 123 may be an isotropic material, where the durometer hardness of the material correlates to a compressive modulus and a shear modulus of the material. More specifically, a higher durometer hardness value of the wear-resistant material of the outer layer 123 may correlate to a higher compressive modulus and a higher shear modulus of the wear-resistant material. Conversely, a lower durometer hardness value of the wear-resistant material of the outer layer 123 may correlate to a lower compressive modulus and a lower shear modulus of the wear-resistant material. The wear-resistant material of the outer layer 123 may be selected to have a higher durometer hardness than the resilient material of the inner layer 121, so that the wear-resistant material of the outer layer may reduce the wear on the fiber contact region 120 caused by contact with the optical fiber 104.

When the fiber contact region 120 includes both an outer layer 123 and an inner layer 121, as depicted in FIGS. 5A-5C, the resilient material of the inner layer and the wear-resistant material of the outer layer 123 may be selected so that the overall durometer hardness of the fiber contact region 120 is less than or equal to about 40 Shore A. The overall hardness of the fiber contact region 120 may result as a combination of the durometer hardness and thickness of the inner layer 121 and the outer layer 123, and the hardness of the outer circumference 105 of the capstan 201. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

In embodiments, the inner layer 121 and the outer layer 123 may comprise materials including without limitation, elastomers, thermoplastic polymers, polyurethane, nylon and the like.

Figure 6C:
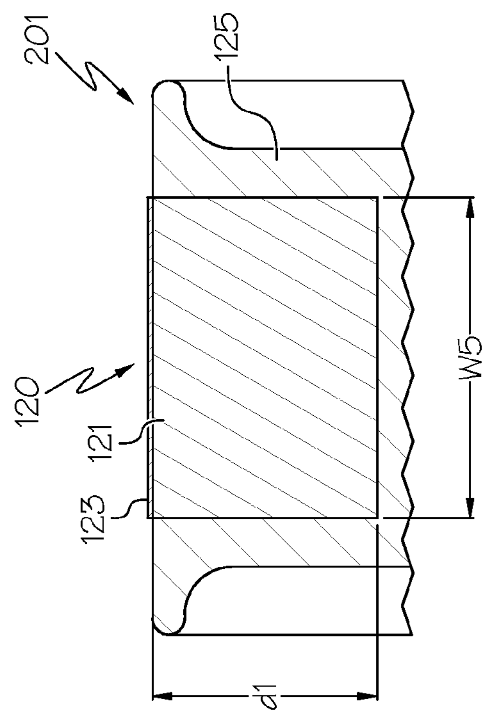
FIG. 6C schematically depicts an enlarged view of a portion of a cross-section of a capstan according to one or more embodiments shown or described herein.
Figure 6B:
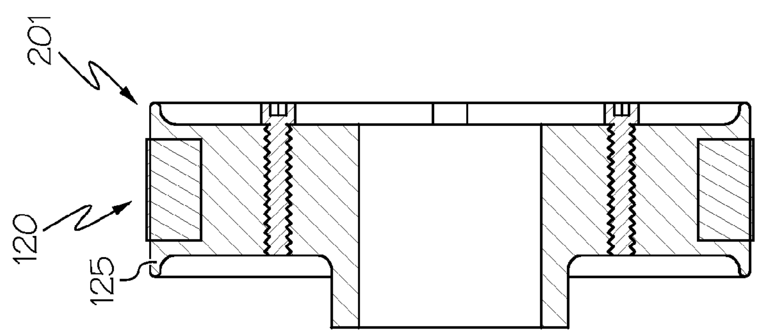
FIG. 6B schematically depicts a front-view cross section of a capstan according to one or more embodiments shown or described herein.
Figure 6A:
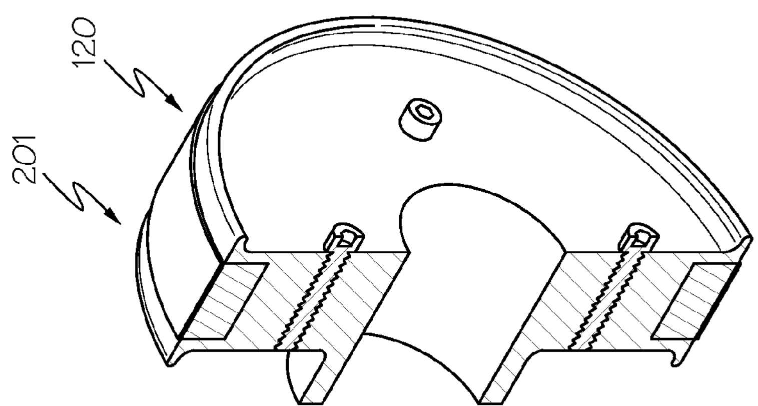
FIG. 6A schematically depicts a perspective cross-sectional view of a capstan according to one or more embodiments shown or described herein.

Referring now to FIGS. 6A, 6B, and 6C, another embodiment of the capstan 201 is schematically depicted. In this embodiment, the fiber contact region 120 of the capstan 201 has a durometer hardness of less than or equal to about 40 Shore A, as described above. However, in this embodiment, the fiber contact region 120 of the capstan 201 includes a channel 125 extending radially inward from the outer circumference 105 of the capstan 201. The channel 125 may have a depth dl extending radially inward from the outer circumference 105 of the capstan 201, and a width W3 extending across the outer circumference 105 of the capstan 201. The depth dl may be selected to be greater than or equal to 1 mm and less than or equal to 12 mm. In an alternative embodiment, the depth dl may be selected to be greater than or equal to about 1 mm and less than or equal to about 5 mm. The inner layer 121 of the fiber contact region 120 may be positioned within the channel 125 of the capstan 201. The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

In one embodiment, a vacuum suction may be applied to the channel 125 to retain the inner layer 121 within the channel 125. The vacuum suction may be applied to the channel 125 by mechanisms including, without limitation, a one-way valve positioned on the capstan 201, the one-way valve in fluid communication with the channel 125. As the capstan 201 rotates, the vacuum suction may counteract a centrifugal force to retain the inner layer 121 within the channel 125. By positioning the inner layer 121 within a channel 125 and utilizing a force, such as a vacuum suction, to retain the inner layer 121 within the channel 125, the inner layer 121 may be prevented from coming free of the fiber contact region 120 because of a centrifugal force cause by the rotation of the capstan 201.

The fiber contact region 120 may optionally include an outer layer 123. The outer layer 123 of the fiber contact region 120 may be positioned over the inner layer 121 of the fiber contact region 120 such that the outer layer 123 encloses the channel 125 of the capstan 201. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes both an outer layer 123 and an inner layer 121, as described above with respect to FIGS. 5A-5C, the resilient material of the inner layer and the wear-resistant material of the outer layer 123 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

Figure 7C:
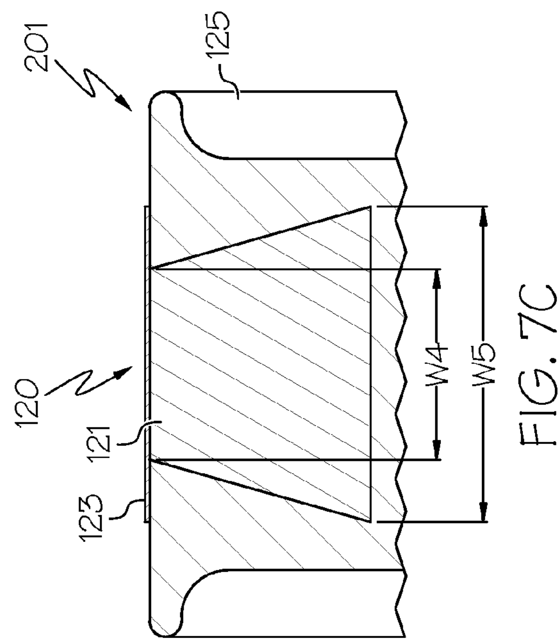
FIG. 7C schematically depicts an enlarged view of a portion of a cross-section of a capstan according to one or more embodiments shown or described herein.
Figure 7B:
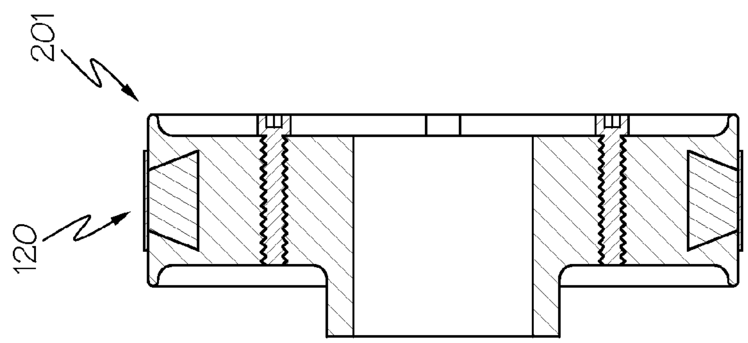
FIG. 7B schematically depicts a front-view cross section of a capstan according to one or more embodiments shown or described herein.
Figure 7A:
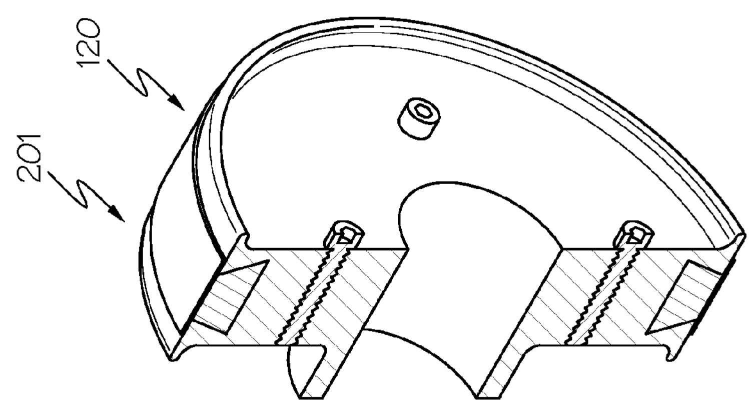
FIG. 7A schematically depicts a perspective cross-sectional view of a capstan according to one or more embodiments shown or described herein.

Referring now to FIGS. 7A, 7B, and 7C, another embodiment of the capstan 201 is schematically depicted. The fiber contact region 120 of the capstan 201 has a durometer hardness of less than or equal to about 40 Shore A, as described above. However, in this embodiment, the fiber contact region 120 of the capstan 201 includes a channel 125 extending radially inward from the outer circumference 105 of the capstan 201. The channel 125 has a width W4 at a position proximate to the outer circumference 105 of the capstan 201, and a width W5 at a position radially inward from the outer circumference 105 of the capstan 201. The channel 125 may be tapered, such that the width W4 of the channel 125 at the outer circumference 105 is less than the width W5 is at a position of the channel 125 radially inward from the outer circumference 105 of the capstan 201. The inner layer 121 of the fiber contact region 120 may be positioned within the channel 125 of the capstan 201. The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

By tapering the width of the channel 125, the shape of the channel 125 may prevent a centrifugal force caused by the rotation of the capstan 201 from causing the inner layer 121 to come free from the channel 125 of the capstan 201.

The fiber contact region 120 may optionally include an outer layer 123 positioned over the inner layer 121 of the fiber contact region 120 such that the outer layer 123 encloses the channel 125 of the capstan 201, as described with respect to FIGS. 6A-6C. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes both an outer layer 123 and an inner layer 121, as described above with respect to FIGS. 5A-5C, the resilient material of the inner layer and the wear-resistant material of the outer layer 123 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

Figure 8C:
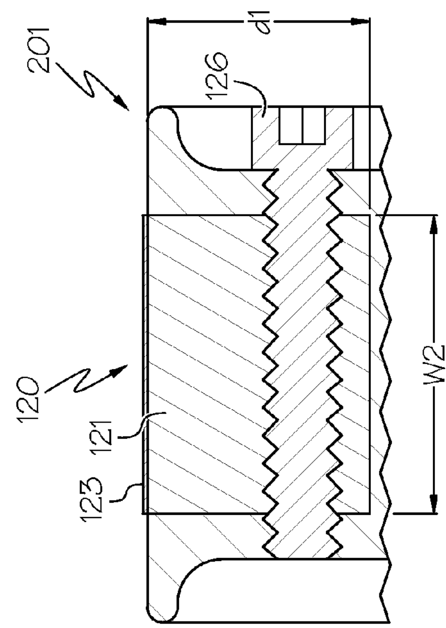
FIG. 8C schematically depicts an enlarged view of a portion of a cross-section of a capstan according to one or more embodiments shown or described herein.
Figure 8B:
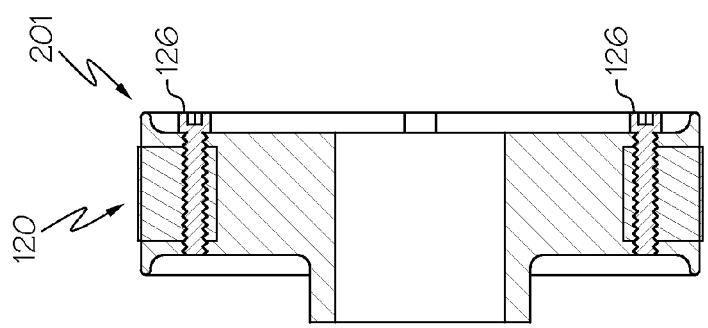
FIG. 8B schematically depicts a front-view cross section of a capstan according to one or more embodiments shown or described herein.
Figure 8A:
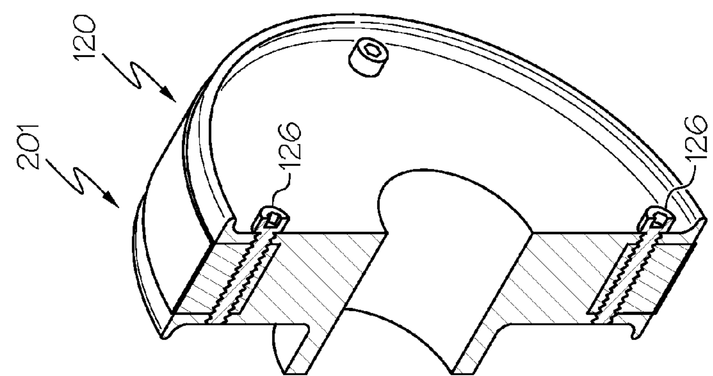
FIG. 8A schematically depicts a perspective cross-sectional view of a capstan according to one or more embodiments shown or described herein.
Figure 9C:
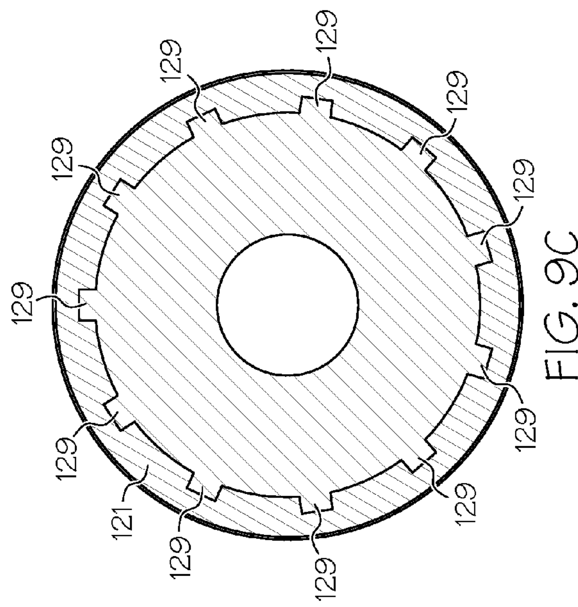
FIG. 9C schematically depicts a section-view of a capstan according to one or more embodiments shown or described herein.
Figure 9D:
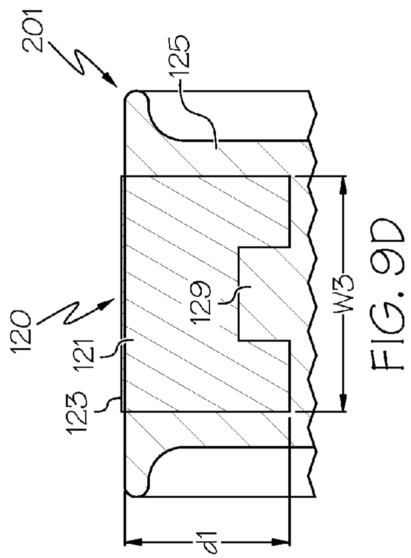
FIG. 9D schematically depicts an enlarged view of a portion of a cross-section of a capstan according to one or more embodiments shown or described herein.
Figure 9B:
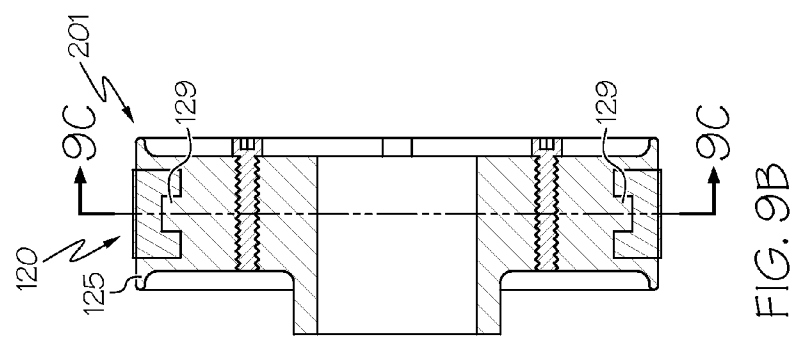
FIG. 9B schematically depicts a front-view cross section of a capstan according to one or more embodiments shown or described herein.
Figure 9A:
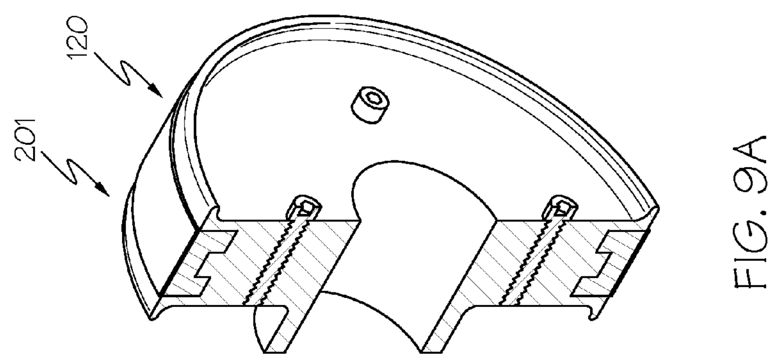
FIG. 9A schematically depicts a perspective cross-sectional view of a capstan according to one or more embodiments shown or described herein.
Figure 10C:
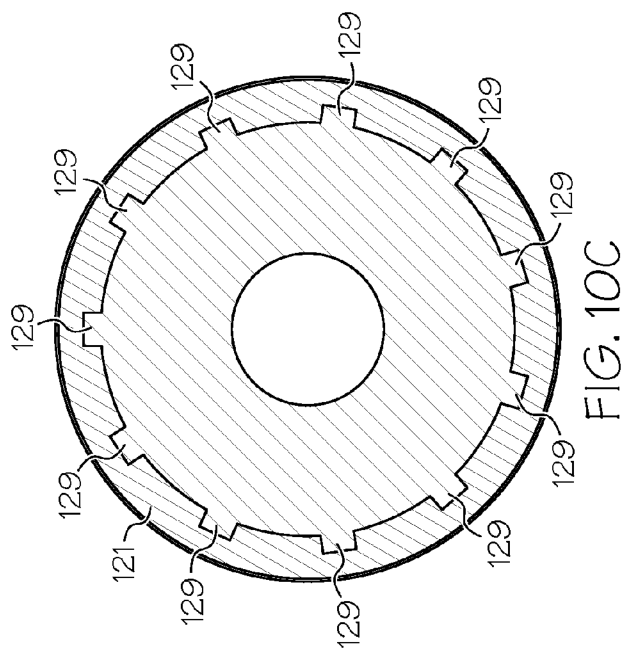
FIG. 10C schematically depicts a section-view of a capstan according to one or more embodiments shown or described herein.
Figure 10D:
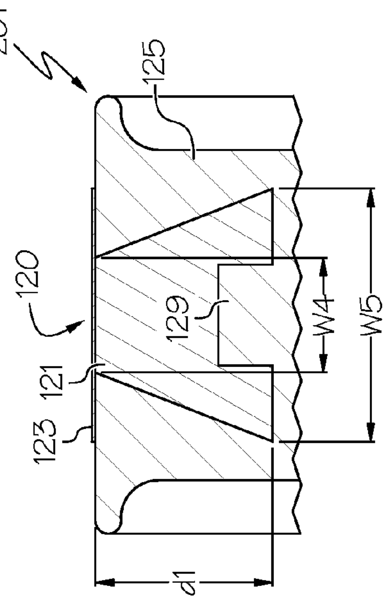
FIG. 10D schematically depicts an enlarged view of a portion of a cross-section of a capstan according to one or more embodiments shown or described herein.
Figure 10B:
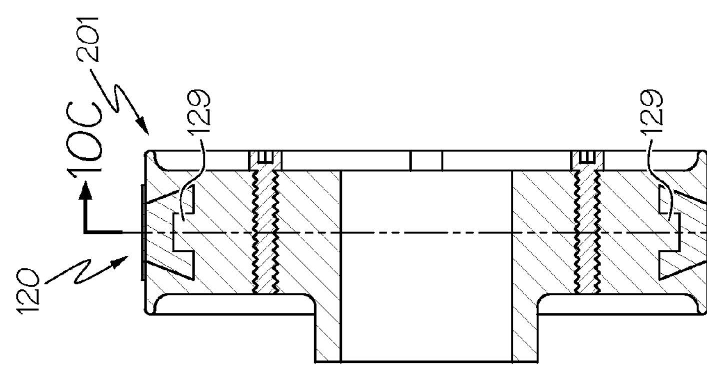
FIG. 10B schematically depicts a front-view cross section of a capstan according to one or more embodiments shown or described herein.
Figure 10A:
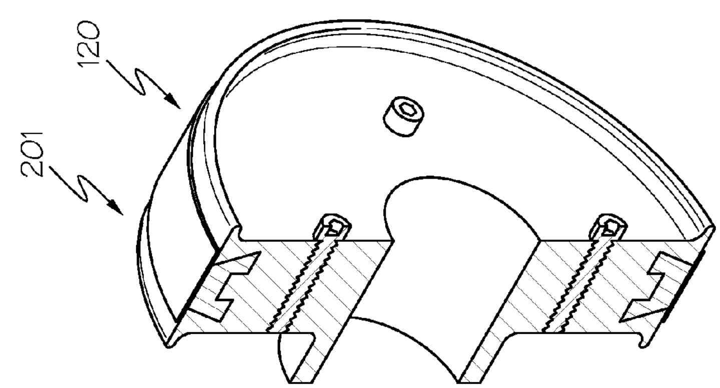
FIG. 10A schematically depicts a perspective cross-sectional view of a capstan according to one or more embodiments shown or described herein.

Referring now to FIGS. 8A, 8B, and 8C, another embodiment of the capstan 201 is schematically depicted. The fiber contact region 120 of the capstan 201 has a durometer hardness of less than or equal to about 40 Shore A, as described above. However, in this embodiment, the fiber contact region 120 of the capstan 201 includes a channel 125 extending radially inward from the outer circumference 105 of the capstan 201. The channel 125 may have a depth dl extending radially inward from the outer circumference 105 of the capstan 201, and a width W2 extending across the outer circumference 105 of the capstan 201. The inner layer 121 of the fiber contact region 120 may be positioned within the channel 125 of the capstan 201. The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

At least one fastener 126 is positioned through the channel 125 and the inner layer 121 of the capstan 201. The at least one fastener may prevent a centrifugal force caused by the rotation of the capstan 201 from causing the inner layer 121 to come free from the channel 125 of the capstan 201. The fastener 126 may include, without limitation, a bolt, a screw, a pin or the like.

The fiber contact region 120 may optionally include an outer layer 123 positioned over the inner layer 121 of the fiber contact region 120 such that the outer layer 123 encloses the channel 125 of the capstan 201, as described with respect to FIGS. 6A-6C. The outer layer 123 of the fiber contact region 120 may be positioned over the inner layer 121 of the fiber contact region 120 such that the outer layer 123 encloses the channel 125 of the capstan 201. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes both an outer layer 123 and an inner layer 121, as described above with respect to FIGS. 5A-5C, the resilient material of the inner layer and the wear-resistant material of the outer layer 123 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

Referring now to FIGS. 9A, 9B, 9C, and 9D another embodiment of the capstan 201 is schematically depicted. In this embodiment, the fiber contact region 120 of the capstan 201 has a durometer hardness of less than or equal to about 40 Shore A, as described above. However, in this embodiment, the fiber contact region 120 of the capstan 201 includes a channel 125 extending radially inward from the outer circumference 105 of the capstan 201, and the capstan includes at least one cog 129 positioned within the channel 125. The channel 125 may have a depth dl extending radially inward from the outer circumference 105 of the capstan 201, and a width W3 extending across the outer circumference 105 of the capstan 201, as described with respect to FIGS. 6A-6C. The depth dl may be selected to be greater than or equal to 1 mm and less than or equal to 12 mm. In an alternative embodiment, the depth dl may be selected to be greater than or equal to about 1 mm and less than or equal to about 5 mm, as described with respect to FIGS. 6A-6C. The inner layer 121 of the fiber contact region 120 may be positioned within the channel 125 of the capstan 201. The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

The capstan 201 includes at least one cog 129 positioned within the channel 125. The at least one cog 129 is positioned within the channel 125, extending radially outward toward the outer circumference 105 of the capstan 201 and engaging the inner layer 121. By engaging the inner layer 121, the at least one cog 129 may retain the position of the inner layer 121, preventing the inner layer from rotating with respect to the capstan 201 when the fiber contact region 120 contacts an optical fiber.

In one embodiment, a vacuum suction may be applied to the channel 125 to retain the inner layer 121 within the channel 125, as described above with respect to FIGS. 6A-6C. The vacuum suction may be applied to the channel 125 by mechanisms including, without limitation, a one-way valve positioned on the capstan 201, the one-way valve in fluid communication with the channel 125. As the capstan 201 rotates, the vacuum suction may counteract a centrifugal force to retain the inner layer 121 within the channel 125. By positioning the inner layer 121 within a channel 125 and utilizing a force, such as a vacuum suction, to retain the inner layer 121 within the channel 125, the inner layer 121 may be prevented from coming free of the fiber contact region 120 because of a centrifugal force cause by the rotation of the capstan 201.

The fiber contact region 120 may optionally include an outer layer 123. The outer layer 123 of the fiber contact region 120 may be positioned over the inner layer 121 of the fiber contact region 120 such that the outer layer 123 encloses the channel 125 of the capstan 201. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes both an outer layer 123 and an inner layer 121, as described above with respect to FIGS. 5A-5C, the resilient material of the inner layer and the wear-resistant material of the outer layer 123 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

Referring now to FIGS. 10A, 10B, 10C, and 10D another embodiment of the capstan 201 is schematically depicted. The fiber contact region 120 of the capstan 201 has a durometer hardness of less than or equal to about 40 Shore A, as described above. However, in this embodiment, the fiber contact region 120 of the capstan 201 includes a channel 125 extending radially inward from the outer circumference 105 of the capstan 201, and the capstan 201 includes at least one cog 129 positioned within the channel 125. The channel 125 has a width W4 at a position proximate to the outer circumference 105 of the capstan 201, and a width W5 at a position radially inward from the outer circumference 105 of the capstan 201, as described with respect to FIGS. 7A-7C. The channel 125 may be tapered, such that the width W4 of the channel 125 at the outer circumference 105 is less than the width W5 is at a position of the channel 125 radially inward from the outer circumference 105 of the capstan 201, as described with respect to FIGS. 7A-7C. The inner layer 121 of the fiber contact region 120 may be positioned within the channel 125 of the capstan 201. The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

By tapering the width of the channel 125, the shape of the channel 125 may prevent a centrifugal force caused by the rotation of the capstan 201 from causing the inner layer 121 to come free from the channel 125 of the capstan 201.

The capstan 201 includes at least one cog 129 positioned within the channel 125, as described above with respect to FIGS. 9A-9D. The at least one cog 129 is positioned within the channel 125, extending radially outward toward the outer circumference 105 of the capstan 201 and engaging the inner layer 121, as described above with respect to FIGS. 9A-9D. By engaging the inner layer 121, the at least one cog 129 may retain the position of the inner layer 121, preventing the inner layer from rotating with respect to the capstan 201 when the fiber contact region 120 contacts an optical fiber.

The fiber contact region 120 may optionally include an outer layer 123 positioned over the inner layer 121 of the fiber contact region 120 such that the outer layer 123 encloses the channel 125 of the capstan 201, as described with respect to FIGS. 6A-6C. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes both an outer layer 123 and an inner layer 121, as described above with respect to FIGS. 5A-5C, the resilient material of the inner layer and the wear-resistant material of the outer layer 123 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced.

Figure 11C:
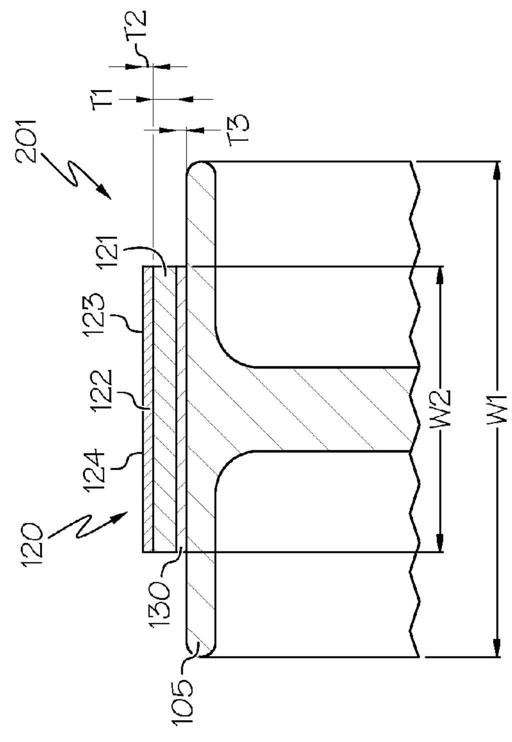
FIG. 11C schematically depicts an enlarged view of a portion of a cross-section of a capstan according to one or more embodiments shown or described herein.
Figure 11B:
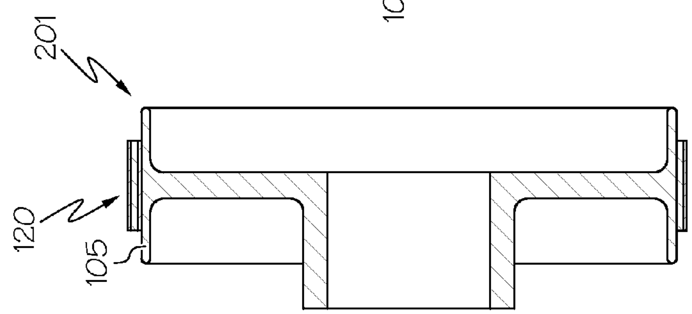
FIG. 11B schematically depicts a front-view cross section of a capstan according to one or more embodiments shown or described herein.
Figure 11A:
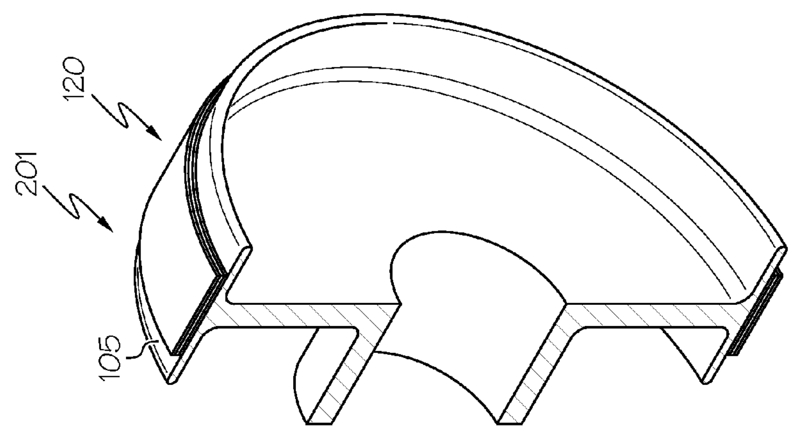
FIG. 11A schematically depicts a perspective cross-sectional view of a capstan according to one or more embodiments shown or described herein.

Referring now to FIGS. 11A, 11B, and 11C, another embodiment of the capstan 201 is schematically depicted. In this embodiment, the fiber contact region 120 of the capstan 201 has a durometer hardness of less than or equal to about 40 Shore A, as described above. However, in this embodiment, the fiber contact region 120 of the capstan 201 includes a base layer 130 positioned on the outer circumference 122 of the capstan 201.

In embodiments, the base layer 130 is positioned over the outer circumference 122 of the capstan 201. The inner layer 121 is positioned over and bonded to the base layer 130. To bond the inner layer 121 to the base layer 130, the inner layer 121 and the base layer 130 may be directly bonded to one another, or the inner layer 121 and the base layer 130 may be fastened by an adhesive or the like. The base layer 130 has a thickness T3 extending radially outward from the outer circumference 122 of the capstan 201 to the inner layer 121. In embodiments, the thickness T3 of the base layer 130 may be greater than or equal to about 0.5 mm and less than or equal to about 2.0 mm. In another embodiment, the thickness T3 of the base layer 130 may be greater than or equal to about 0.5 mm and less than or equal to about 1.0 mm.

In embodiments, the base layer 130 may be formed from an inflexible material. The inflexible material of the base layer 130 may be selected to have a desired hardness and a desired compressive and shear modulus to counteract a centrifugal force acting on the base layer 130 and the inner layer 121. In embodiments, the inflexible material of the base layer 130 is selected to have a hardness less than or equal to about 90 Shore A. In another embodiment, the inflexible material of the base layer 130 is selected to have a hardness less than or equal to about 53 Shore D.

Similar to the inner layer 121 as described above with respect to FIGS. 5A-5C, the inflexible material of the base layer 130 may be an isotropic material, where the durometer hardness of the material correlates to a compressive modulus and a shear modulus of the material. More specifically, a higher durometer hardness value of the inflexible material of the inner layer 130 may correlate to a higher compressive modulus and a higher shear modulus. Conversely, a lower durometer hardness value of the inflexible material of the base layer 130 may correlate to a lower compressive modulus and shear modulus. As will be described in greater detail herein, a relatively high durometer hardness value, and consequently a high compressive and shear modulus of the inflexible material may assist in resisting centrifugal force acting on the base layer 130 and the inner layer 121 bonded to the base layer 130.

In embodiments, the inflexible material of the base layer 130 may be selected to have a shear modulus and a compressive modulus of less than or equal to about 150 MPa. In another embodiment, the inflexible material of the base layer 130 may be selected to have a shear and compressive modulus less than or equal to about 145 MPa. By selecting the inflexible material of the base layer 130 to have a durometer hardness of less than or equal to about 150 MPa, the base layer 130 may resist plastic deformation resulting from a centrifugal force applied to the base layer 130 as a result of the rotation of the capstan 201.

In embodiments, the base layer 130 may comprise materials including without limitation, elastomers, thermoplastic polymers, polyurethane, nylon and the like.

The inner layer 121 may be formed from a resilient material having a durometer hardness of less than or equal to about 35 Shore A, as described above with respect to FIGS. 5A-5C. In another embodiment, the resilient material may be selected to have a durometer hardness of less than or equal to about 20 Shore A, as described above with respect to FIGS. 5A-5C. As referenced above with respect to FIGS. 5A-5C, a low durometer hardness value of the resilient material of the inner layer 121 may reduce the compressive and shear stress in the optical fiber 104 in contact with the fiber contact region 120, as will be described in greater detail herein.

The resilient material of the inner layer 121 may also be selected to have a shear modulus and a compressive modulus of less than or equal to about 1 MPa, as described with respect to FIGS. 5A-5C. In another embodiment, the resilient material of the inner layer may be selected to have a shear modulus and a compressive modulus greater than or equal to about 0.1 MPa and less than or equal to about 0.5 MPa, as described above with respect to FIGS. 5A-5C. By selecting the resilient material of the inner layer 121 to have a shear modulus and a compressive modulus of less than or equal to about 1 MPa, the inner layer 121 of the fiber contact region 120 may elastically deform under the compressive force and tensile force applied by the optical fiber 104. In another embodiment, the resilient material of the inner layer 121 may be selected to have the same compressive modulus and shear modulus as the primary coating 114 of the optical fiber 104 directed over the fiber conveyance pathway 101, as described with respect to FIGS. 5A-5C.

The fiber contact region 120 may optionally include an outer layer 123. The outer layer 123 of the fiber contact region 120 may be positioned over the inner layer 121 of the fiber contact region 120 such that the outer layer 123 encloses the channel 125 of the capstan 201. The outer layer 123 may be formed from a wear-resistant material having a durometer hardness of greater than or equal to about 55 Shore A and less than or equal to about 90 Shore A, as described above with respect to FIGS. 5A-5C. In another embodiment, the outer layer 123 may be selected to have a durometer hardness greater than or equal to about 65 Shore A and less than or equal to about 80 Shore A, as described above with respect to FIGS. 5A-5C. As described above with respect to FIGS. 5A-5C, by including an outer layer 123 formed from a wear-resistant material, the structural integrity of the fiber contact region 120 may be maintained, and wear on the inner layer 121 from contact with an optical fiber directed over the fiber conveyance pathway may be reduced.

When the fiber contact region 120 includes an outer layer 123, an inner layer 121, and a base layer 130, the resilient material of the inner layer, the wear-resistant material of the outer layer 123, and the material of the base layer 130 may be selected so that the overall durometer hardness of the fiber contact region 120 is less than or equal to about 40 Shore A. By including an outer layer 123 formed from a wear-resistant material, the structural integrity of the fiber contact region 120 may be maintained, and wear on the inner layer 121 from contact with an optical fiber 104 directed over the fiber conveyance pathway 101 may be reduced. By including a base layer 130 formed from an inflexible material which is bonded to the resilient material of the inner layer 121, the base layer 130 may resist a centrifugal force acting on the base layer 130 and the inner layer 121. By resisting the centrifugal force, the base layer 130 may assist in retaining the position of the inner layer 121 on the capstan 201.

Figure 12:
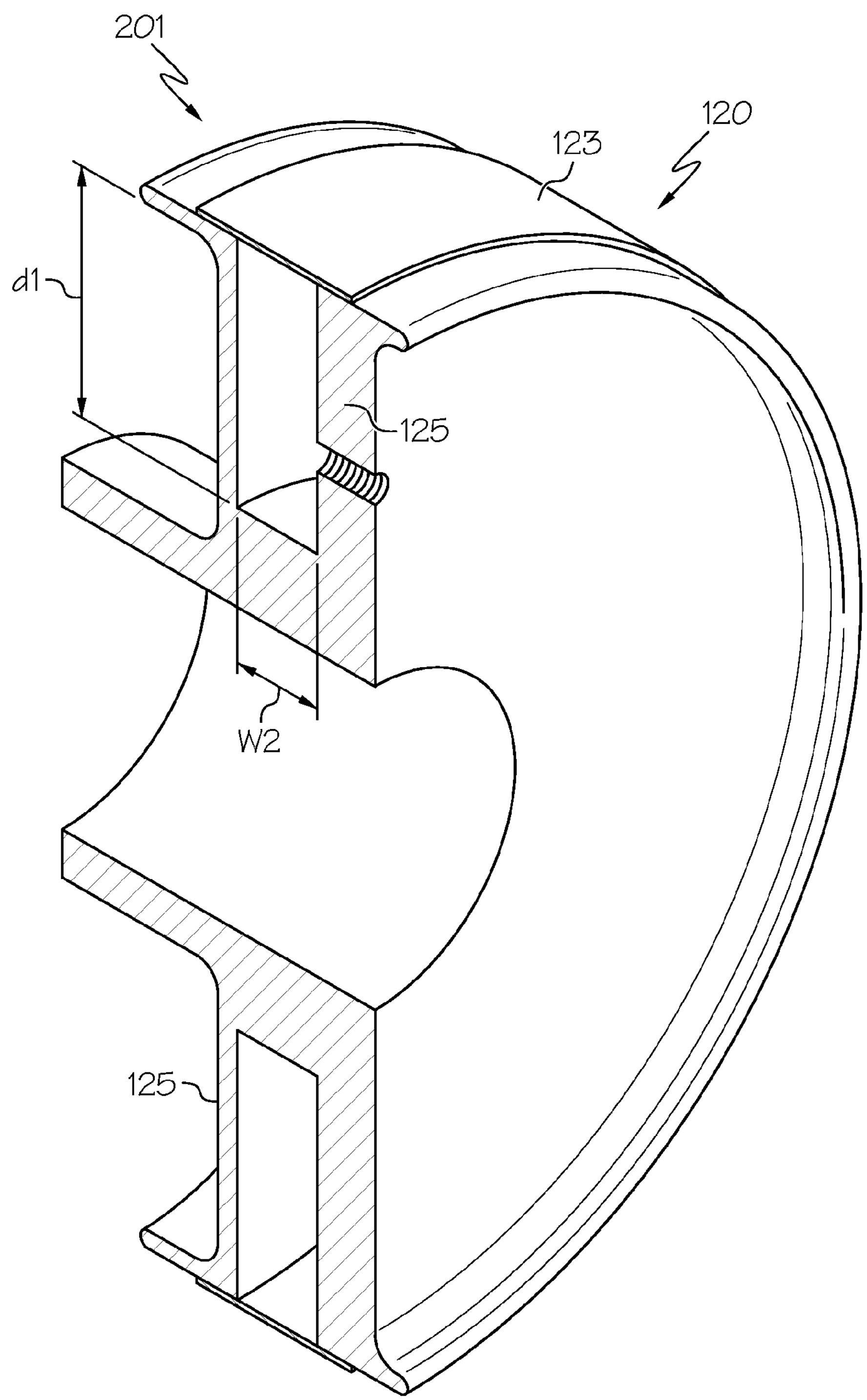
FIG. 12 schematically depicts a perspective cross-sectional view of a capstan according to one or more embodiments shown or described herein.

Referring to FIG. 12, another embodiment of the capstan 201 is depicted. The fiber contact region 120 of the capstan 201 has a durometer hardness of less than or equal to about 40 Shore A, as described above. However, in this embodiment, the capstan 201 includes a channel 125 extending radially inward from the outer circumference 105 of the capstan 201. The channel 125 may have a depth dl extending radially inward from the outer circumference 105 of the capstan 201, and a width W2 extending across the outer circumference 105 of the capstan 201. The width W2 may be greater than or equal to about ten times a diameter of an optical fiber 104 directed over the fiber conveyance pathway 101, as described with respect to FIGS. 5A-5C. An outer layer 123 of the fiber contact region 120 may be positioned over the channel 125, enclosing the channel 125 to form an enclosed chamber. However, in this embodiment, an inner layer 121 is not positioned in the channel 125, and the channel 125 is unfilled.

The outer layer 123 may be formed from a wear-resistant material having a durometer hardness of greater than or equal to about 55 Shore A and less than or equal to about 90 Shore A, as described above with respect to FIGS. 5A-5C.

In this embodiment, a pressure may be applied within the channel 125 so that the pressure is exerted against the outer layer 123 such that the fiber contact region exhibits a durometer hardness of less than about 40 Shore A. The pressure may be applied within the channel by mechanisms including, without limitation, a one-way valve positioned on the capstan 201, the one-way valve in fluid communication with the channel 125.

While specific reference has been made herein to embodiments of the capstan 201 of the screen testing apparatus 100, it should be understood that the first capstan 102 and the second capstan 106 of the screen testing apparatus may be similarly configured to include a fiber contact region 120 according to the embodiments described herein.

Figure 13:
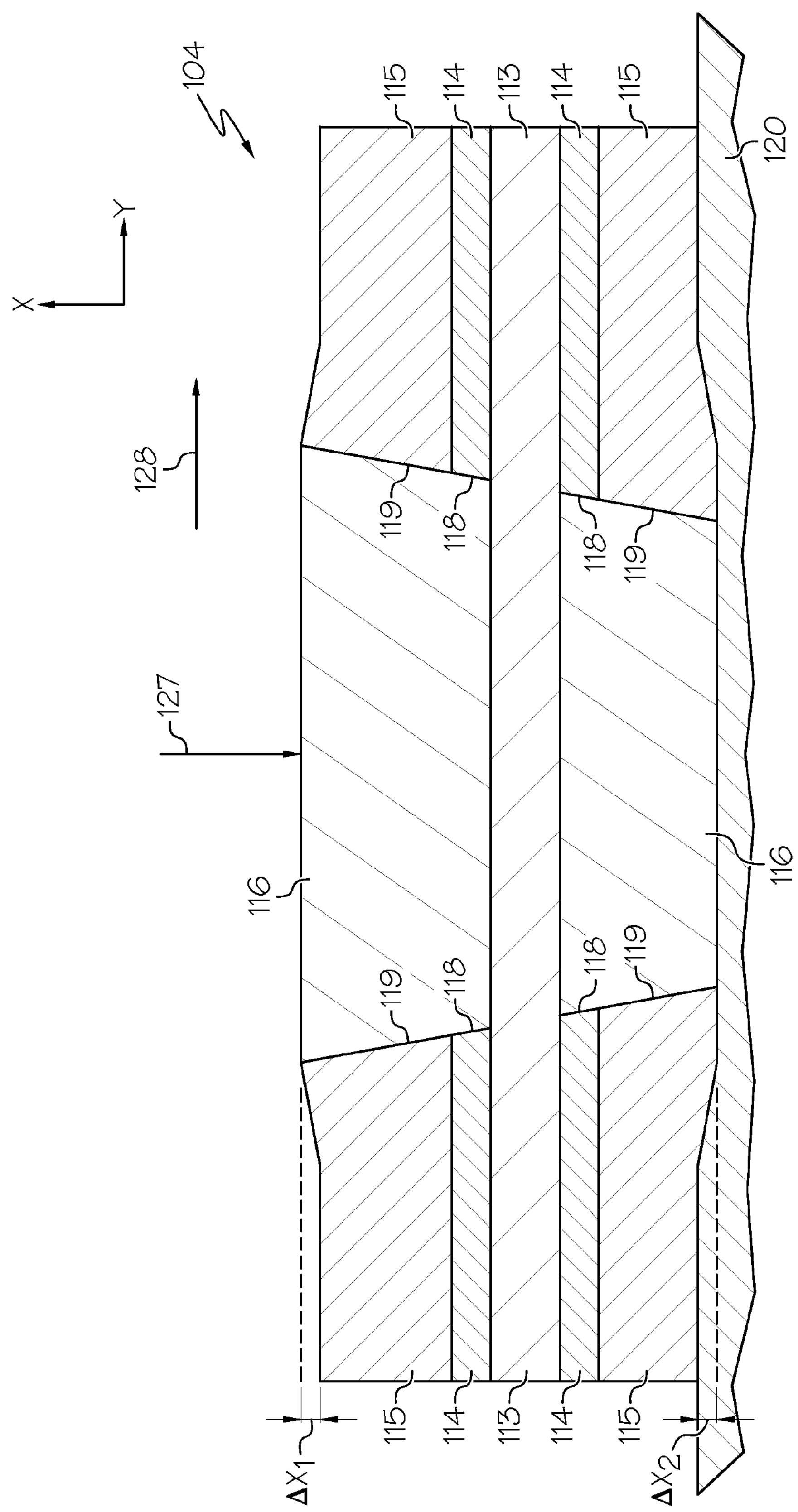
FIG. 13 schematically depicts a cross-section view of a coated optical fiber directed over a fiber conveyance pathway under compressive stress according to one or more embodiments shown or described herein.

As described and depicted hereinabove, various embodiments of the fiber contact region 120 of the capstan 201 to reduce the compressive and shear stress placed on the optical fiber 104 during the screen testing process are disclosed. Referring to FIG. 13, a cross section of an optical fiber 104 directed over a capstan including a fiber contact region 120 according to one or more or the embodiments described herein is schematically depicted. The optical fiber 104 is depicted under a compressive force 127, such as the compressive force applied to the optical fiber 104 by the first pinch belt 103 as the first pinch belt 103 impinges the optical fiber 104 against the fiber contact region 120 of the capstan 201. The fiber contact region 120 elastically deforms a distance ΔX2 under the compressive force applied to the optical fiber 104, allowing the high modulus re-coat coating 116 of the optical fiber to depress into the fiber contact region 120. Because the fiber contact region 120 elastically deforms under the compressive force applied to the optical fiber 104, the difference in the amount of deflection ΔX1 between the portion of the optical fiber 104 including a re-coat coating 116 and the portion of the optical fiber 104 including a primary coating 114 is reduced. Because the difference in the amount of deflection is reduced, the stress at the interface 118 between the primary coating 114 and the re-coat coating 116 is reduced, which may decrease the likelihood of cohesive failure between the primary coating 114 and the re-coat coating 116 at the interface 118.

Figure 14:
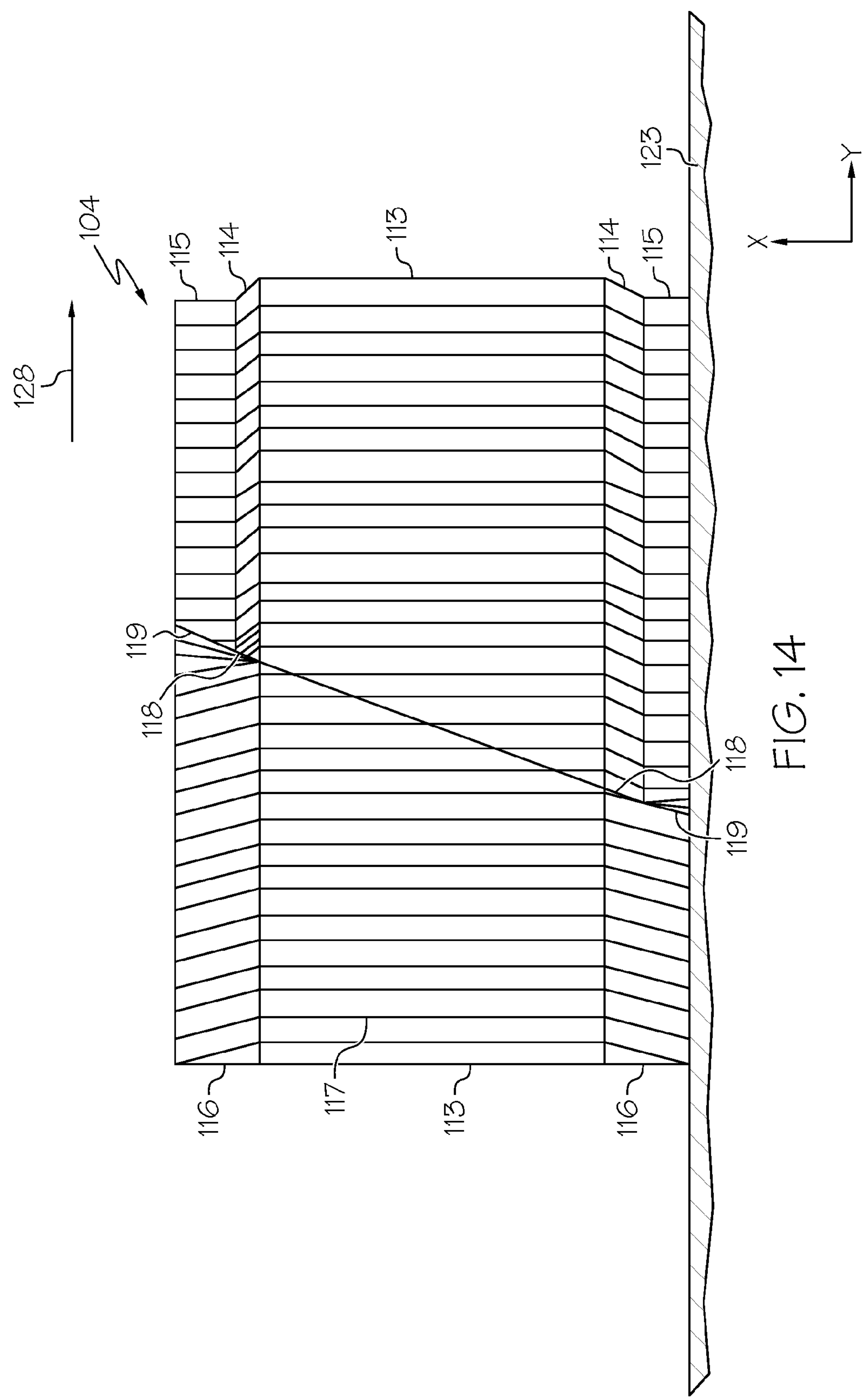
FIG. 14 schematically depicts a cross-section view of a coated optical fiber directed over a fiber conveyance pathway under shear stress according to one or more embodiments shown or described herein.

Referring to FIG. 14, an optical fiber is schematically depicted under shear stress, such as the shear stress applied to the optical fiber 104 by the screen testing apparatus 100 at the capstan 201, with the capstan 201 including a fiber contact region 120 according to one or more or the embodiments described herein. The fiber contact region 120 elastically deforms under the shear force applied to the optical fiber 104, reducing the elastic deformation in the primary coating 114 of the optical fiber 104. Because the elastic deformation in the primary coating 114 of the optical fiber 104 is reduced, the difference in the amount of deflection between the portion of the optical fiber 104 including a re-coat coating 116 and the portion of the optical fiber 104 including a primary coating 114 is reduced. As the difference in the amount of deflection is reduced, the stress, and accordingly the strain illustrated by lines 117 at the interface 118 between the primary coating 114 and the re-coat coating 116 is reduced. Because the stress at the interface 118 between the primary coating 114 and the re-coat coating 116 is reduced, the likelihood of cohesive failure between the primary coating 114 and the re-coat coating 116 at the interface 118 may decrease.

Accordingly, by including a capstan with a fiber contact region having a desired hardness and compressive and shear modulus, the stress imparted on the coatings of an optical fiber during a screen test process may be reduced. Further, by including a wear-resistant outer layer over a resilient inner layer, the stress imparted on the coatings of the optical fiber may be reduced, while the wear on the fiber contact region from contact with the optical fiber may be minimized.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. An apparatus for screen testing an optical fiber, the apparatus comprising:

a fiber conveyance pathway;

a capstan having an outer circumference and a fiber contact region extending around the outer circumference, the fiber contact region having an overall durometer hardness of less than or equal to 40 Shore A, wherein the capstan is positioned adjacent to the fiber conveyance pathway such that when the optical fiber is directed over the fiber conveyance pathway, the optical fiber engages with the fiber contact region of the capstan; and a pinch belt positioned adjacent to the fiber conveyance pathway such that the fiber conveyance pathway extends between at least a portion of the pinch belt and the fiber contact region of the capstan, wherein the pinch belt is engageable with the fiber contact region of the capstan such that, when the optical fiber is directed over the fiber conveyance pathway, the optical fiber is impinged between the pinch belt and the fiber contact region of the capstan.

2. The apparatus for screen testing an optical fiber of claim 1 wherein the fiber contact region comprises an inner layer of resilient material having a durometer hardness of less than or equal to 35 Shore A.

3. The apparatus for screen testing an optical fiber of claim 2, wherein the inner layer of resilient material has a shear modulus and a compressive modulus of less than or equal to 1 MPa.

4. The apparatus for screen testing an optical fiber of claim 2, wherein the fiber contact region further comprises an outer layer positioned over the inner layer of resilient material, the outer layer having a durometer hardness of less than or equal to 90 Shore A.

5. The apparatus for screen testing an optical fiber of claim 4, wherein the outer layer has a durometer hardness greater than or equal to 55 Shore A and less than or equal to 90 Shore A.

6. The apparatus for screen testing an optical fiber of claim 4, wherein the outer layer has a thickness greater than or equal to 10 microns and less than or equal to 300 microns.

7. The apparatus for screen testing an optical fiber of claim 4, wherein the fiber contact region further comprises a base layer positioned beneath the inner layer of resilient material, wherein the base layer is bonded to the inner layer of resilient material, the base layer having a durometer hardness of less than or equal to 90 Shore A.

8. The apparatus for screen testing an optical fiber of claim 2, wherein a compressive modulus and a shear modulus of the fiber contact region is substantially the same as a compressive modulus and a shear modulus of a primary coating of the optical fiber directed over the fiber conveyance pathway.

9. The apparatus for screen testing an optical fiber of claim 1, wherein the capstan further comprises a channel extending radially inward from the outer circumference of the capstan, and the fiber contact region comprises an outer layer positioned over the channel of the capstan, the outer layer covering the channel to form an enclosed chamber on the capstan.

10. The apparatus for screen testing an optical fiber of claim 9, wherein the fiber contact region further comprises an inner layer of resilient material having a durometer hardness of less than or equal to 35 Shore A, the inner layer of resilient material positioned within the channel of the capstan beneath the outer layer.

11. The apparatus for screen testing an optical fiber of claim 10, wherein the capstan further comprises at least one cog positioned within the channel.

12. The apparatus for screen testing an optical fiber of claim 10, wherein the channel of the capstan is tapered, such that a width of the channel is narrower at the outer circumference of the capstan than at a position radially inward from the outer circumference.

13. The apparatus for screen testing an optical fiber of claim 10, wherein vacuum suction is utilized to retain the inner layer of resilient material in the channel of the capstan.

14. The apparatus for screen testing an optical fiber of claim 9, wherein the enclosed chamber is pressurized such that the chamber exerts a force on the outer layer.

15. The apparatus for screen testing an optical fiber of claim 9, wherein the fiber contact region has a width that is less than 10 times a diameter of the optical fiber directed over the fiber conveyance pathway.

16. An apparatus for screen testing an optical fiber, the apparatus comprising:

a fiber conveyance pathway;

a capstan having an outer circumference and a fiber contact region extending around the outer circumference, the fiber contact region having an overall durometer hardness of less than or equal to 40 Shore A, the fiber contact region comprising;

an inner layer of resilient material positioned on the outer circumference of the capstan;

an outer layer of wear-resistant material positioned over the inner layer of resilient material, the outer layer of wear-resistant material having a durometer hardness of less than or equal to 90 Shore A; and a pinch belt positioned adjacent to the fiber conveyance pathway such that the fiber conveyance pathway extends between at least a portion of the pinch belt and the fiber contact region of the capstan, wherein the pinch belt is engageable with the fiber contact region of the capstan such that, when the optical fiber directed over the fiber conveyance pathway, the optical fiber is impinged between the pinch belt and the fiber contact region of the capstan.

17. The apparatus for screen testing an optical fiber of claim 16, wherein the inner layer of resilient material has a shear modulus and a compressive modulus of less than or equal to 1 MPa.

18. The apparatus for screen testing an optical fiber of claim 16, wherein the outer layer of wear-resistant material has a thickness greater than or equal to 10 microns and less than or equal to 300 microns.

19. The apparatus for screen testing an optical fiber of claim 16, wherein the capstan further comprises a channel extending radially inward from the outer circumference of the capstan, wherein the inner layer of resilient material positioned within the channel beneath the outer layer of wear-resistant material, and the outer layer of wear-resistant material covering the channel to form an enclosed chamber on the capstan.

* * * * *